(12) United States Patent
Benameur et al.

(10) Patent No.: US 6,652,865 B2
(45) Date of Patent: Nov. 25, 2003

(54) METHOD AND FORMULATION FOR DECREASING STATIN METABOLISM

(75) Inventors: Hassan Benameur, Genas-Azieu (FR); Vincent Jannin, Lyons (FR); Delphine Roulot, Riverie (FR)

(73) Assignee: Gattefosse Holding, Saint Priest (FR)

( * ) Notice: Subject to any disclaimer, the term of this patent is extended or adjusted under 35 U.S.C. 154(b) by 6 days.

(21) Appl. No.: 09/935,277

(22) Filed: Aug. 22, 2001

(65) Prior Publication Data

US 2003/0086948 A1 May 8, 2003

(30) Foreign Application Priority Data

Jul. 27, 2001 (FR) .............................. 01 10094

(51) Int. Cl.[7] .................. A61K 9/00; A01N 25/00
(52) U.S. Cl. .................. 424/400; 424/400; 424/405; 424/439; 424/450; 424/497; 424/498; 424/499
(58) Field of Search ................... 424/499, 498, 424/400, 405, 497, 439

(56) References Cited

U.S. PATENT DOCUMENTS 6,054,136 A * 4/2000 Farah et al. ................. 424/400
6,248,363 B1 * 6/2001 Patel et al. .................. 424/497

FOREIGN PATENT DOCUMENTS

EP          0 670 715 B1     7/1997 .......... A61K/9/107

OTHER PUBLICATIONS

Vincent F. Mauro "Clinical Pharmacokinetics and Practical Applications of Simvastatin" *Clin. Pharmacokinet* 24, 195–202 (1993).

Rau et al. "Pharmacokinetics and Drug Disposition—Grapefruit juice—terfenadine single–dose interaction: Magnitude, mechanism, and relevance" *Clin. Pharm. & Ther.* 61, 401–409 (1997).

Du Souich et al. "Contribution f the Small Intestine to the First–Pass Uptake and Systemic Clearance of Propranolol in Rabbits" *Drug Metab.* and *Disp.* 23, 279–284 (1995).

* cited by examiner

Primary Examiner—Carlos A. Azpuru
Assistant Examiner—Micah Paul Young
(74) Attorney, Agent, or Firm—Heslin Rothenberg Farley & Mesiti P.C.

(57) ABSTRACT

A pharmaceutical composition for oral use is disclosed. It includes, as active principle, a drug liable to undergo a strong first intestinal passage effect and a carrier which is self-micro-emulsifying on contact with an aqueous phase. The carrier includes:

a therapeutically effective amount of the active principle;

a lipophilic phase, which is a mixture of glycerol mono-, di- and triesters and of PEG mono- and diesters with at least one fatty acid chosen from the group comprising $C_8$–$C_{18}$ fatty acids;

a surfactant phase which is a mixture of glycerol mono-, di- and triesters and of PEG mono- and diesters with caprylic acid ($C_8$) and capric acid ($C_{10}$);

a co-surfactant phase which is an ester of a polyvalent alcohol with at least one fatty acid chosen from the group comprising caprylic esters of propylene glycol, lauric esters of propylene glycol and oleic esters of polyglycerol. A method of decreasing the effect of intestinal metabolism on a drug using the composition is also disclosed.

9 Claims, 2 Drawing Sheets

US 6,652,865 B2

METHOD AND FORMULATION FOR DECREASING STATIN METABOLISM

CROSS REFERENCE TO RELATED APPLICATIONS

This application claims the priority of French application 01.10094, filed Jul. 27, 2001, the entire disclosure of which is incorporated herein by reference.

FIELD OF THE INVENTION

The invention relates to pharmaceutical methods and oral compositions.

BACKGROUND OF THE INVENTION

It is known from the documents Drug Metab. Disp. (1 995) 23: 279–84 and Transplantation (1992) 53: 596–602 that intestinal metabolism plays an important role in the bioavailability of a certain number of drugs or active principles. Thus, studies have shown that the bioavailability of an active principle can be improved by blocking or reducing the intestinal metabolism [see Clin. Pharmacol. Ther. (1997) 61: 401–9] rather than by acting on the metabolism of the liver. The solution consisting in blocking the intestinal metabolism has a certain risk since it acts directly on the regulatory system. Specifically, cellular transporters have a well-defined role whose regulation depends on the concentration of ligands in the lumen. If, for example, the ligand concentration decreases, the number of transporters increases.

The Applicant has thus sought to reduce the intestinal metabolism which a certain number of molecules undergo.

SUMMARY OF THE INVENTION

The invention relates to pharmaceutical methods and oral compositions comprising an active principle liable to undergo a large first intestinal passage effect. Although the invention concerns all active principles liable to undergo a first intestinal passage effect, this effect is described more particularly in relation to the statins and especially simvastatin, without, however, this being limiting.

The compositions of the invention are in the form of systems that are self-microemulsifying on contact with an aqueous phase. The systems comprise:
  a therapeutically effective amount of the active principle;
  a lipophilic phase comprising a mixture of glycerol mono-, di- and triesters and of PEG mono- and diesters with at least one fatty acid chosen from the group comprising $C_8$–$C_{18}$ fatty acids;
  a surfactant phase comprising a mixture of glycerol mono-, di- and triesters and of PEG mono- and diesters with caprylic acid ($C_8$) and capric acid ($C_{10}$);
  a co-surfactant phase comprising at least one ester of an alcohol with at least one fatty acid chosen from the group comprising caprylic esters of propylene glycol, lauric esters of propylene glycol and oleic esters of polyglycerol,
  the ratio SA/CoSA being between 0.2 and 6.

DETAILED DESCRIPTION OF THE INVENTION

Figure 1:
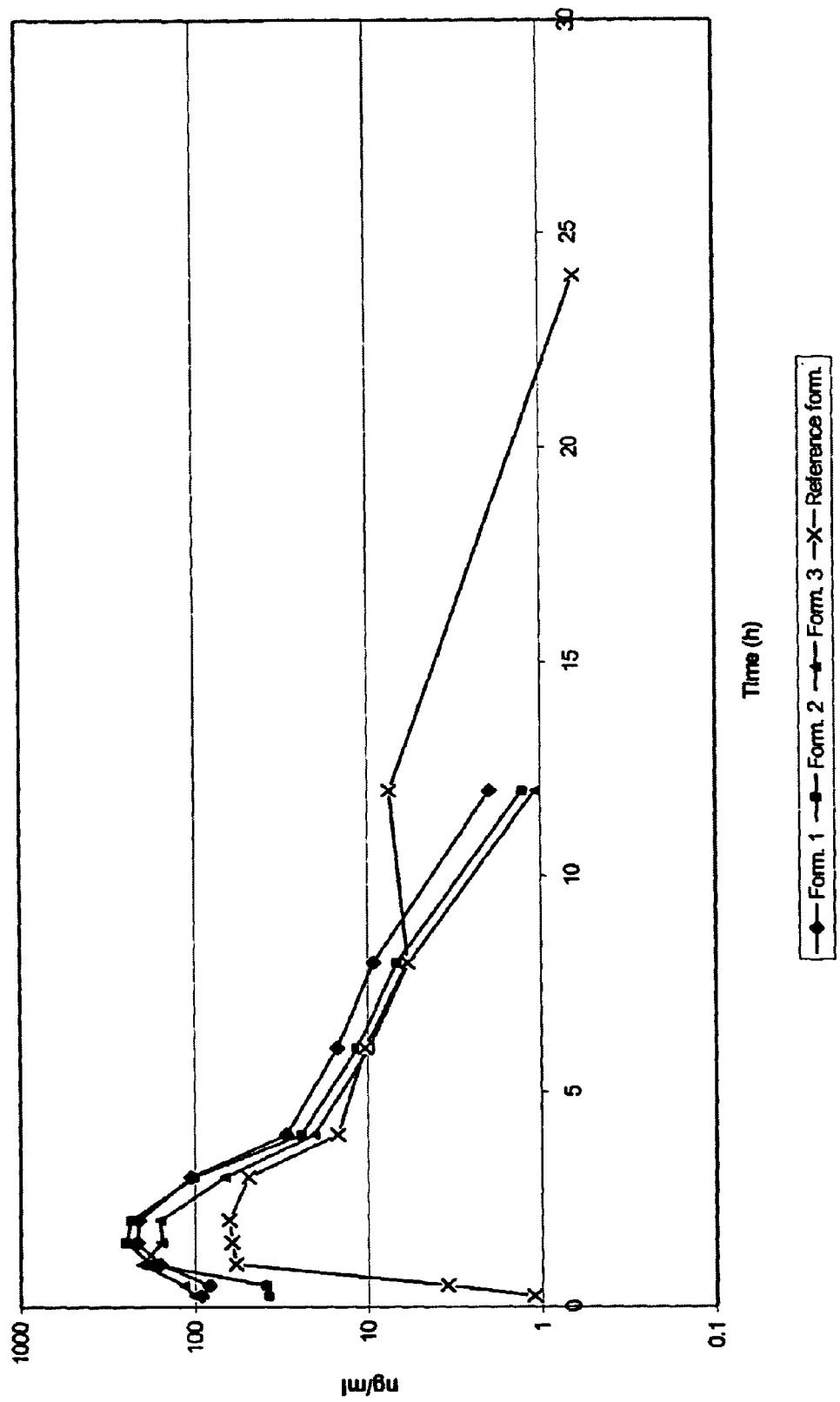
FIG. 1 represents the average concentration of simvastatin in the plasma as a function of time.

The statins constitute a therapeutic family which acts by inhibiting hydroxymethylglutaryl (HMG) Coenzyme A-reductase, an enzyme which limits the synthesis of cholesterol in the liver and stimulates the activity of the LDL (Low Density Lipoprotein) receptors. As a result of this mechanism of action, statins are essentially used as hypocholesterolemic agents. A certain number of studies have moreover demonstrated that statins have a preventive effect on cardiovascular diseases, and also that they induce a regression of atheromatous plaques. There are at present six statins, which are, respectively, lovastatin, pravastatin, fluvastatin, atorvastatin, cerivastatin and, finally, simvastatin, which is more particularly illustrated in the description hereinbelow.

Simvastatin is a product obtained by synthesis from the fermentation product of *Aspergillus terreus*. This molecule, which is well known, of empirical formula $C_{25}H_{38}O_5$, is a lactone whose activity is triggered by means of the enzymatic or chemical opening reaction of its lactone function. In practice, simvastatin is made active by hydroxylation to the β-hydroxy acid. Physically, simvastatin is in the form of a white crystalline powder which is virtually insoluble in water but highly soluble in chloroform, methanol and ethanol. After oral administration, simvastatin is hydrolysed after absorption in the intestine and the liver to its β-hydroxy acid form, its main metabolite, which is the source of the competitive and reversible inhibitory effect on HMG CoA-reductase.

Although simvastatin is absorbed in the gastrointestinal tract, it is known to undergo hepatic metabolism. The hepatic metabolism is primarily via cytochrome CYP 3A4. This phenomenon is described in particular in document Clin. Pharmacokinet 24(3): 195–202, 1993, which indicates that the systemic bioavailability of simvastatin is only 7% of the dose ingested. A solution for improving the bioavailability of simvastatin is to inhibit the action of cytochrome CYP 3A4 with inhibitors such as itraconazole, detoconazole or grapefruit juice. However, this solution is unsatisfactory since it may lead, as already stated, to a deregulation of the metabolism. The Applicant has also found that simvastatin undergoes a strong first intestinal passage effect, a problem which, a priori, was not previously known for this molecule. A strong first intestinal passage effect is reflected in systemic bioavailability below 50%, often below 30%, and in this case below 10%.

Consequently, the problem which the invention proposes to solve is that of improving the systemic bioavailability of active principles liable to undergo a strong first intestinal passage effect by minimizing this effect rather than by blocking it. To do this, the invention provides a pharmaceutical composition for oral use in the form of a system which is self-microemulsifying on contact with an aqueous phase, the said system comprising:
  a therapeutically effective amount of the said active principle;
  a lipophilic phase comprising a mixture of glycerol mono-, di- and triesters and of PEG mono- and diesters with at least one fatty acid chosen from the group comprising $C_8$–$C_{18}$ fatty acids;
  a surfactant phase comprising a mixture of glycerol mono-, di- and triesters and of PEG mono- and diesters with caprylic acid ($C_8$) and capric acid ($C_{10}$);
  a co-surfactant phase comprising at least one ester of an alcohol with at least one fatty acid chosen from the group comprising caprylic esters of propylene glycol, lauric esters of propylene glycol and oleic esters of polyglycerol, the ratio SA/CoSA being between 0.2 and 6.

The self-microemulsifying systems which are of concern in the invention are known under the name SMEDDS®, a trade mark registered by Gattefossé meaning Self Micro Emulsifying Drug Delivery System, and are described more particularly in document EP-A-670 715 and the corresponding document U.S. Pat. No. 6,054,136. The Applicant has found, equally surprisingly and unexpectedly, that the constituents of the SMEDDS® make it possible to reduce the intestinal metabolism of the active principle.

In the above mentioned documents, it is indicated that, as a result of the formation of the microemulsion on contact with an aqueous phase, SMEDDS® enable water-insoluble active principles to be dissolved, and consequently instantaneously by presenting them in the form of a multiparticulate supramolecular structure. The abovementioned documents therefore describe only the problem of solubility of the active principles, which is improved by the SMEDDS® formulation. However, no reference is made anywhere in these documents to the action of SMEDDS® on metabolism, in particular on intestinal metabolism. Thus, the Applicant has found, entirely surprisingly, that the incorporation of an active principle with a strong first intestinal passage effect into a self-microemulsifying system makes it possible to reduce the first intestinal passage effect, and thus to improve the systemic bioavailability of the active molecule. The availability of the active molecule in the liver is greater and the systemic passage is thus proportionally greater. The action does not therefore take place downstream (in the liver) but rather upstream (in the intestine).

The SMEDDS® may be, at ambient temperature, in solid or liquid form depending on the nature of the fatty substances of which they are composed. Thus, if at least one fatty substance constituting the SMEDDS® has a melting point higher than ambient temperature, about 25° C., then the SMEDDS® will be solid at ambient temperature. On the contrary, if at least one fatty substance constituting the SMEDDS® has a melting point of less than about 25° C., then the SMEDDS® is liquid at ambient temperature. Consequently, the SMEDDS® may be incorporated into gel capsules in liquid form, optionally while hot, and then, depending on the nature of their constituents, remain liquid or become semi-solid at ambient temperature. The manufacturing process is relatively simple since it consists in mixing together all the constituents, including the active principle, with or without heating depending on the physicochemical characteristics of the fatty substances.

In the description hereinbelow and in the claims:
the expression "aqueous phase" denotes:
either the in vivo physiological medium as it presents itself after ingesting the composition, and the pH of which varies as a function of the state of the gastrointestinal tract,
or a reconstituted in vitro physiological medium, the microemulsion then being formed on simple contact with the aqueous phase, without ingestion,
all the percentages are given on a weight basis.

According to a first characteristic of the composition of the invention, the lipophilic phase comprises a mixture of glycerol mono-, di- and triesters and of PEG mono- and diesters with at least one fatty acid chosen from the group comprising saturated and unsaturated $C_8$–$C_{18}$ fatty acids.

In practice, this mixture is obtained by an alcoholysis reaction of polyethylene glycol with a molecular weight of between 300 and 1500 and of a hydrogenated plant oil itself consisting of a mixture in variable proportions, depending on its nature, of mono-, di- and triglycerides of at least one of the fatty acids described above. This same mixture may also be obtained by esterifying glycerol and PEG with a molecular weight of between 300 and 1500 with at least one of the fatty acids described above, or alternatively by mixing esters of glycerol and ethylene oxide condensates with at least one of the said fatty acids.

In practice, the lipophilic phase has an HLB value of less than 20, preferably between 9 and 15, and represents between 1% and 99% by weight of the composition. In a first embodiment, the lipophilic phase predominantly comprises a mixture of glycerol mono-, di- and triesters and of PEG mono- and diesters with the combination of saturated $C_8$–$C_{18}$ fatty acids, has an HLB value equal to 14 and represents between 50% and 95% by weight of the composition. In practice, such a mixture is obtained by an alcoholysis reaction of PEG with a molecular weight of between 300 and 1500 with an oil predominantly containing lauric triglycerides. A product corresponding to this definition is Gelucire® 44/14 sold by Gattefossé. This product is fully defined in the 3rd edition of the European Pharmacopoeia under the definition lauric macrogolglycerides.

In a second embodiment, the lipophilic phase comprises a mixture of glycerol mono-, di- and triesters and of PEG mono- and diesters with saturated and unsaturated $C_{16}$–$C_{18}$ fatty acids. Products corresponding to this definition are the products Labrafil M1944CS and Labrafil M2125CS sold by Gattefossé and in accordance with the monographs of the 3rd edition of the European Pharmacopoeia under the respective names "Oleoyl Macrogolglycerides" and "Linoleoyl Macrogolglycerides".

Moreover and as already stated, the surfactant phase comprises a mixture of glycerol mono-, di- and triesters and of PEG mono-, di- and triesters with caprylic acid and capric acid.

The surfactant phase may be obtained in the same manner as previously, by alcoholysis reaction starting with polyethylene glycol with a molecular weight of between 200 and 600 and a hydrogenated plant oil fraction which is rich in glycerol ester, with caprylic acid and capric acid. The surfactant phase may also be obtained by esterifying glycerol and polyethylene glycol with capric acid and caprylic acid, but also by mixing an ester of glycerol and ethylene oxide condensates with caprylic acid and capric acid. In practice, the surfactant phase has an HLB value of between 5 and 20.

A product corresponding to the definition of the surfactant phase is the product sold by Gattefossé under the brand name Labrasol®, which corresponds to the monograph of the 3rd edition of the European Pharmacopoeia entitled "magrogol glyceride caprylocapric [caprylocapric magrogol glyceride]". In one advantageous embodiment, the surfactant phase represents between 1% and 30% by weight of the composition.

Moreover, and as already stated, the co-surfactant phase comprises at least one ester of an alcohol with at least one fatty acid.

The monoesters of propylene glycol chosen from the group comprising propylene glycol monocaprylate and propylene glycol monolaurate are more particularly preferred. The products sold by Gattefossé and containing monoesters of propylene glycol and of caprylic acid are Capryol® 90 and Capryol® PGMC. Similarly, a product sold by Gattefossé and containing propylene glycol monolaurate is Lauroglycol 90®.

In a first embodiment, the co-surfactant phase contains propylene glycol monocaprylate and represents between 3% and 32% by weight of the composition.

In a second embodiment, the co-surfactant phase contains propylene glycol monolaurate and represents between 1% and 8% by weight of the composition. In this case, Lauroglycol® 90 is advantageously used.

As already stated, the self-microemulsifying system as described above makes it possible to reduce the first intestinal passage effect of a certain number of active principles such as, for example, those belonging to the statin family, in particular simvastatin. Consequently, and in one particular embodiment, the statin is simvastatin. Moreover, to be therapeutically effective, the simvastatin represents between 0.1% and 6% by weight of the composition and advantageously 4% by weight.

The invention also relates to a pharmaceutical composition for oral use comprising simvastatin as active principle, this composition being characterized in that it is in the form of a system which is self-microemulsifying on contact with an aqueous phase, comprising by weight (mg/g):

between 0.1% and 6% of simvastatin, between 52% and 70% of Gelucire® 44/14, between 5% and 30% of Labrasol®, between 15% and 30% of propylene glycol monocaprylate.

In a first embodiment, the propylene glycol monocaprylate contained in this composition consists of Capryol® PGMC representing between 15% and 25% by weight of the composition. In a second embodiment, the monocaprylate consists of Capryol® 90 and represents between 20% and 30% by weight of the composition.

In one preferred form, the composition of the invention comprises:

4% of simvastatin, 65.2% of Gélucire® 44/14, 10.3% of Labrasol®, 20.5% of Capryol PGMC.

Alternatively, the composition comprises:

4% of simvastatin, 57.6% of Gélucire® 44/14, 12.8% of Labrasol®, 25.6% of Capryol® 90.

The invention also relates to a pharmaceutical composition for oral use icomprising simvastatin as active principle, this composition being characterized in that it is in the form of a system which is self-microemulsifying on contact with an aqueous phase, comprising by weight (in mg/g):

0.1% to 6% of simvastatin, between 52% and 70% of Gélucire® 44/14, between 6% and 30% of Labrasol®, between 1% and 8% of Lauroglycol® 90.

Advantageously, the composition of the invention contains:

4% of simvastatin, 65.3% of Gélucire(® 44/14, 24.6% of Labrasol®, 6.1% of Lauroglycol® 90.

The invention and the advantages arising therefrom will emerge more clearly from the following preparation example in support of the attached figures.

EXAMPLE 1

The following three formulations are manufactured:

| COMPONENTS | FORMULA 1 | FORMULA 2 | FORMULA 3 |
|---|---|---|---|
| SIMVASTATIN | 4.0% | 4.0% | 4.0% |
| LABRASOL | 10.3% | 12.8% | 24.6% |
| GÉLUCIRE ® 44/14 | 65.2% | 57.6% | 65.3% |
| CAPRYOL ® PGMC | 20.5% | — | — |
| CAPRYOL ® 90 | — | 25.6% | — |
| LAUROGLYCOL ® 90 | — | — | 6.1% |
| TOTAL | 100% | 100% | 100% |

Each of the constituents of the formulae are mixed together at ambient temperature with stirring at between 60 and 100 rpm.

EXAMPLE 2

Reduction in the intestinal barrier effect with the product which is the subject of the invention, relative to simvastatin alone, using human intestinal microsomes.

The test is carried out in vitro using human intestinal microsomes containing:

20 mg/ml of proteins, 0.09 nmol/mg of cytochromes P450, 0.77 nmol/min/mg of cytochromes P450 3 A 4.

1 mg/ml of microsomes is then placed in contact:

with a regenerating system having the following composition:

| NADPH | 1 mmol |
|---|---|
| Glucose 6-phosphate dehydrogenase | 2 units/ml |
| Glucose 6-phosphate | 10 mmol |
| Potassium phosphate, pH 7.4 | 100 mmol |
| Magnesium chloride | 10 mmol | followed by equilibration at 37° C. for 3 minutes.

The reaction is then initiated by adding 12 µmol of simvastatin or of the composition of the invention to the reaction mixture. 100 µl aliquots are mixed with a solution of 400 µl of a 50/50 mixture of ice and acetonitrile at 0, 15, 30, 60, 120 and 180 minutes. Testosterone is tested in parallel as control component.

The level of simvastatin remaining is then quantified by HPLC and mass spectrometry.

The conditions for carrying out the HPLC are as follows:

| Column | Hypersil BDS C18, 30 × 2 mm i.d., 3 µm, |
|---|---|
| Buffer | 25 mmol of ammonium hydroxide adjusted to a pH of 3.5 with formic acid, |
| mobile phase | A-10% of buffer and 90% of water, B-10% of buffer and 90% of acetonitrile, |
| Gradient | 0% of B to 100% of B over 3 minutes, re-equilibration for 2 minutes, |
| flow rate | 300 µl/min |
| Injection volume | 10 µl |

The mass spectrometer used is known under the reference PE SCIEX 150.

The results are given in the following table. After 15 minutes, the testosterone has completely disappeared from the cell medium. On the other hand, for the three compositions of the invention, between 20% and 23% of simvastatin remains in the irculation despite the first intestinal passage effect.

| | PERCENTAGE REMAINING Time in min | | | | | |
|---|---|---|---|---|---|---|
| Test product | 0 | 15 | 30 | 60 | 120 | 180 |
| TESTOSTERONE | 100 | — | — | — | — | 0 |
| SIMVASTATIN | 100 | 0 | 0 | 0 | 0 | 0 |
| FORMULA 1 | 100 | 20.4 | 2.66 | 0.13 | 0.07 | 0.22 |
| FORMULA 2 | 100 | 21.1 | 2.00 | 0.12 | 0.03 | 0.08 |
| FORMULA 3 | 100 | 22.6 | 2.29 | 0.14 | 0.06 | 0.13 |

EXAMPLE 3

Comparison of the relative bioavailabilities in vivo between formulae 1, 2 and 3 and a reference formula, namely Zocor®.

To evaluate the influence of various concentrations of the composition of the invention on the relative oral bioavailability of simvastatin, four male Beagle dogs were treated in a crossed model (over 4 periods, one formulation per period and per dog, an interval of one week between each period) with the three formulations 1, 2 and 3 and a reference formulation, ZOCOR® sold by the Laboratoires Merck, Sharp & Dohme-Chibret.

The formulations were administered in the form of capsules, each comprising 40 mg of simvastatin. Each dog received two capsules, thus corresponding to a total dose of 80 mg. The dose administered of 80 mg per dog is assumed to give concentration profiles of simvastatin in the plasma that are comparable to those observed in humans at high therapeutic doses (80 mg).

A blood sample was taken from each dog before the treatment and at successive times of 15 minutes, 30 minutes, 1 hour, 1½ hours, 2 hours, 3 hours, 4 hours, 6 hours, 8 hours, 12 hours and 24 hours. The concentrations of simvastatin and of hydroxysimvastatin in the plasma were determined by HPLC/MS analytical method.

Figure 2:
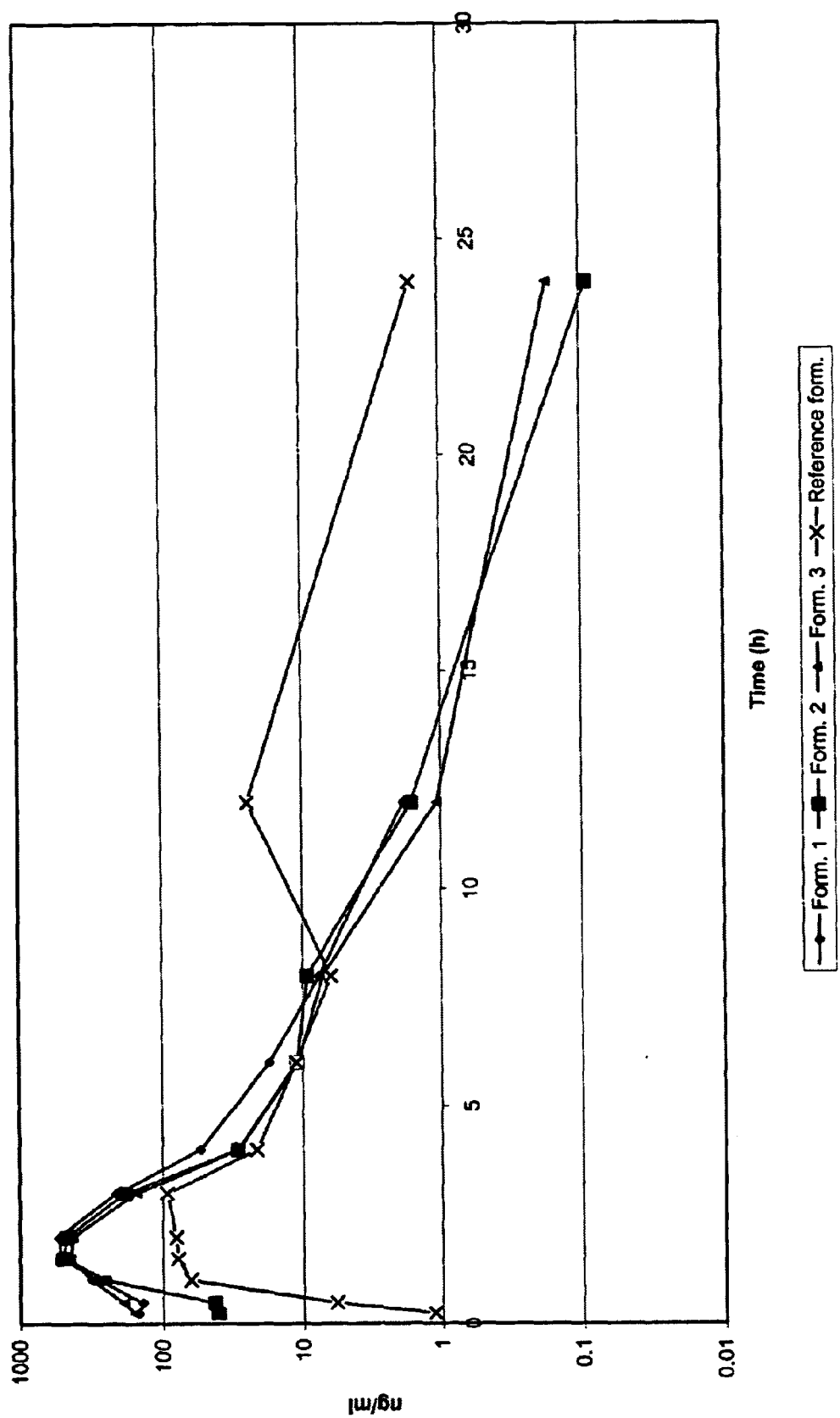
FIG. 2 represents the average concentration of hydroxysimvastatin in the plasma as a function of time.

The results given in FIGS. 1 and 2, which represent the average concentrations of simvastatin (FIG. 1) and of hydroxysimvastatin (FIG. 2) in the plasma as a function of time for the three formulations and the reference formula (ZOCOR®).

After administration of the ZOCOR®, a delay in the absorption of simvastatin is observed. Specifically, simvastatin and hydroxysimvastatin are found in the plasma in all the animals only at and above the third sample, that is to say one hour after administration. In contrast, levels of simvastatin and of hydroxysimvastatin in the plasma are detected from the 15th minute after administration of formulae 1, 2 and 3. In other words, the composition of the invention increases the level of absorption.

The table below gives the average kinetic parameters (Cmax and Tmax) and absorption parameters (Vmax, T50% and T90%) for the reference formula ZOCOR® and formulae 1 to 3. In this table, the parameters have the following meanings:

| Parameters | Reference | Formula 1 | Formula 2 | Formula 3 |
|---|---|---|---|---|
| Cmax | 63.945 | 215.2125 | 249.49 | 203.84 |
| Tmax | 1 | 1.5 | 1 | 0.5 |
| Vmax (% h) | 19.71 | 57.84 | 62.14 | 62.91 |
| T50% (h) | 3 | 1.5 | 1.5 | 1 |
| T90% (h) | 22 | 5 | 3.5 | 3.5 |

Cmax: maximum level in the plasma (ng/ml)
Tmax: time to obtain Cmax (h)
Vmax: maximum level of absorption (% dose/h)
T50%: time to absorb 50% of the dose
T90%: time to absorb 90% of the dose As shown in the above table, the level of absorption is three times as high for the formulae of the invention compared with ZOCOR®. Consequently, a maximum concentration in the plasma for the formulae of the invention which is considerably higher than that of Zocor® is found.

The most significant difference between formulations 1, 2 and 3 and Zocor® concerns the improvement in the absorption. Specifically, after administration of formulation 1, the average area under the curve (AUC for simvastatin and for hydroxysimvastatin) is two to three times greater than the corresponding values for Zocor®.

The table below gives the levels of absorption as a function of time of simuvastatin.

| | Average level of absorption (V) (% of the dose/h) | | | |
|---|---|---|---|---|
| T(h) | Ref. | 1 | 2 | 3 |
| 0 | 0.00 | 0.00 | 0.00 | 0.00 |
| 0.25 | 0.67 | 57.84 | 23.98 | 62.91 |
| 0.5 | 1.72 | 18.06 | 10.65 | 26.67 |
| 1 | 19.71 | 47.56 | 57.13 | 53.14 |
| 1.5 | 12.52 | 48.33 | 62.14 | 26.36 |
| 2 | 13.29 | 40.55 | 45.08 | 33.09 |
| 3 | 8.38 | 18.66 | 16.94 | 11.32 |
| 4 | 2.03 | 3.01 | 2.82 | 2.56 |
| 6 | 2.21 | 3.61 | 2.93 | 2.29 |
| 8 | 1.33 | 2.27 | 1.60 | 1.28 |
| 12 | 1.38 | 0.85 | 0.52 | |
| 24 | 1.01 | | | |

As shown in this table, the rate of absorption of simvastatin is close to 100 times greater for formulae 1 and 3 than for the reference formula. Formulation 3, for its part, shows that the nature of the constituents may be varied and thus the level of absorption may be varied directly. These results therefore demonstrate that an effect is being produced on the rate of dissolution of the active agent.

Moreover, the relative bioequivalence index resulting from the sum of the areas under the curve (AUC for simvastatin and hydroxysimvastatin for formulation 1 versus Zocor®) is 3.26. The relative bioequivalence corresponding to formula 2 is 2.88, and formula 3 is 2.66.

Consequently, even though a small decrease in the relative bioavailability between formulae 1, 2 and 3 is observed, the different concentrations of the components constituting these formulae do not induce a variation in the relative bioavailability of simvastatin in dogs.

What is claimed is:

1. A method of decreasing statin metabolism within intestinal epithelium comprising formulating said statin with a self micro-emulsfying carrier, said self micro-emulsifying carrier comprising:

a lipophilic phase comprising a mixture of glycerol mono-, di- and triesters and of PEG mono- and diesters with at least one fatty acid chosen from the group comprising $C_8$–$C_{18}$ fatty acids;

a surfactant phase comprising a mixture of glycerol mono-, di- and triesters and of PEG mono- and diesters with caprylic acid ($C_8$) and capric acid ($C_{10}$);

a co-surfactant phase comprising at least one ester of a polyvalent alcohol with at least one fatty acid chosen from the group comprising caprylic esters of propylene glycol, lauric esters of propylene glycol and oleic esters of polyglycerol, the ratio SA/CoSA being between 0.2 and 6.

2. A method according to claim 1 wherein said lipophilic phase has an HLB value about 14 and it represents between 50 and 95% by weight of the composition.

3. A method according to claim 1 wherein the surfactant phase represents between 1% and 30% by weight of the mixture.

4. A method according to claim 1 wherein the co-surfactant phase is a monoester of propylene glycol chosen from the group comprising propylene glycol monocaprylate and propylene glycol monolaurate.

5. A method according to claim 4 wherein the surfactant phase contains propylene glycol monocaprylate, and it represents between 3% and 32% by weight of the composition.

6. A method according to claim 4 wherein the co-surfactant phase contains propylene glycol monolaurate and it represents between 1% and 8% by weight of the composition.

7. A method according to claim 1 wherein the statin is simvastatin.

8. A method of decreasing statin metabolism within intestinal epithelium, said method comprising formulating said statin with a self micro-emulsifying carrier, said self micro-emulsifying carrier comprising:

(i) a lipophilic phase comprising a mixture of glycerol mono-, di- and triesters and of PEG mono- and diesters with at least one fatty acid chosen from the group comprising $C_8$–$C_{18}$ fatty acids;

(ii) a surfactant phase comprising a mixture of glycerol mono-, di- and triesters and of PEG mono- and diesters with caprylic acid ($C_8$) and capric acid ($C_{10}$);

(iii) a co-surfactant phase comprising from 3 to 32% by weight of an ester of a polyvalent alcohol with a caprylic ester of propylene glycol, said surfactant and co-surfactant being in a ratio by weight between 0.2 and 6.

9. A method according to claim 8 wherein:

(i) said lipophilic phase comprises from 52 to 70% by weight of lauric macrogolglycerides;

(ii) said surfactant phase comprises from 5 to 30% by weight of caprylocapric magrogol glyceride; and (iii) said co-surfactant phase comprising from 15% to 30% propylene glycol monocaptylate and said statin is simvastatin, comprising from 0.1 to 6% by weight.

* * * * *

UNITED STATES PATENT AND TRADEMARK OFFICE
CERTIFICATE OF CORRECTION

PATENT NO.   : 6,652,865 B2
DATED        : November 25, 2003
INVENTOR(S)  : Benameur et al.

It is certified that error appears in the above-identified patent and that said Letters Patent is hereby corrected as shown below:

Column 10,
Line 27, delete the word "monocaptylate" and insert -- monocaprylate --

Signed and Sealed this

Fourth Day of May, 2004

JON W. DUDAS
*Acting Director of the United States Patent and Trademark Office*